(12) United States Patent
Sakaguchi

(10) Patent No.: US 8,105,303 B2
(45) Date of Patent: Jan. 31, 2012

(54) SHEET MEMBER, HIGH-DENSITY REGION-CONTAINING SHEET MANUFACTURING METHOD AND DISPOSABLE DIAPER USING SHEET MEMBER

(75) Inventor: Satoru Sakaguchi, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 472 days.

(21) Appl. No.: 12/306,714

(22) PCT Filed: Jun. 25, 2007

(86) PCT No.: PCT/JP2007/062710
§ 371 (c)(1),
(2), (4) Date: Dec. 26, 2008

(87) PCT Pub. No.: WO2008/004456
PCT Pub. Date: Jan. 10, 2008

(65) Prior Publication Data
US 2009/0275909 A1    Nov. 5, 2009

(30) Foreign Application Priority Data

Jul. 7, 2006  (JP) ................ 2006-188580

(51) Int. Cl.
*A61F 13/15*  (2006.01)
(52) U.S. Cl. ......... 604/385.16; 604/385.22; 604/385.27; 604/385.26
(58) Field of Classification Search ............ 604/385.16, 604/385.22, 385.27, 385.26
See application file for complete search history.

(56) References Cited

U.S. PATENT DOCUMENTS 4,062,995 A * 12/1977 Korpman ................ 428/134
4,463,045 A *  7/1984 Ahr et al. ................ 428/131
5,824,004 A * 10/1998 Osborn et al. ........ 604/385.04

FOREIGN PATENT DOCUMENTS

| JP | 05-245961 A | 9/1993 |
| JP | 2002-105835 A | 4/2002 |
| JP | 2002-238934 A | 8/2002 |

(Continued)

OTHER PUBLICATIONS

European search report for EP application No. 07767516.3.

(Continued)

*Primary Examiner* — Jacqueline F. Stephens
(74) *Attorney, Agent, or Firm* — Lowe, Hauptman, Ham & Berner, LLP

(57) ABSTRACT

A high-density region-containing sheet having a high-density region and a low-density region, a sheet member produced by joining the high-density region of the high-density region-containing sheet to an elastic member, and a disposable diaper using the sheet member as its chassis are provided. A sheet in a soft state by imparting preheat is pressed between a pair of opposed shaping rolls and having a toothed region and rotatable. Thus, a high-density region-containing sheet where high-density regions and low-density regions are formed is produced. Such two high-density region-containing sheets are joined through an extended elastic member to form a projection/recess pattern. In such a way, a high-density region-containing sheet can be produced. A sheet member in which at least one of two sheets is a high-density region-containing sheet, the high-density regions are joined through an extended elastic member, and a projection/recess pattern can be formed when the elastic member is contracted is produced.

8 Claims, 9 Drawing Sheets

FOREIGN PATENT DOCUMENTS

| | | |
|---|---|---|
| JP | 2003-235894 A | 8/2003 |
| JP | 2006-027089 A | 2/2006 |
| JP | 2008-125917 A | 6/2008 |
| WO | 9513779 A1 | 5/1995 |

OTHER PUBLICATIONS

European Patent Office, Office Communication mailed Oct. 2, 2009.

PCT/JP2007/062710 International Search Report.

\* cited by examiner

SHEET MEMBER, HIGH-DENSITY REGION-CONTAINING SHEET MANUFACTURING METHOD AND DISPOSABLE DIAPER USING SHEET MEMBER

RELATED APPLICATIONS

The present application is based on International Application Number PCT/JP2007/062710 filed Jun. 25, 2007, and claims priority from Japanese Application Number 2006-188580, filed Jul. 7, 2006, the disclosures of which are hereby incorporated by reference herein in their entirety.

TECHNICAL FIELD

The present invention relates to a method of manufacturing a high-density region-containing sheet, a sheet member using the high-density region-containing sheet, and a disposable diaper using the sheet member. Particularly, it relates to a high-density region-containing sheet having high-density regions and low-density regions, a sheet member obtained by attaching the high-density regions of the high-density region-containing sheet to an elastic member, and a disposable diaper using the sheet member for a chassis.

BACKGROUND ART

Conventionally, disposable diapers, for example, have been known as disposable absorbent articles. The disposable diapers have been widely employed for babies and children to elderly persons and physically-handicapped persons, and have replaced reusable absorbent articles made of cloth. In order to enhance both the adhesion to users and cushioning properties, a stretchable composite sheet obtained by affixing two types of non-stretchable sheet members to each other with an elastic member, in an expanded state, having a shape selected from a thread shape, net shape, strip shape, sheet shape, or the like, sandwiched therebetween, to allow a degree of elasticity of a sheet member such as a non-stretchable nonwoven fabric has been used.

In a state where the elastic member in the stretchable composite sheet contracts, each of the sheet members has large wrinkles and pleats formed therein. The wrinkles and the pleats allow cushioning properties to be obtained. However, such large wrinkles and pleats irregularly appear on the nonwoven fabric with a random rigidity distribution of the nonwoven fabric. When the user wears such a disposable diaper, the disposable diaper is inferior in adhesion to the user and does not feel pleasant because a touch sensation is also preceded by feeling of rigidity.

In recent years, it has been reported that when large wrinkles and pleats continue to stimulate the skin, they affect the body as a tactile stimulus, which causes not only a feeling of discomfort but also an endocrine function and an autonomic imbalance and affects even intellectual development. Thus, there has been an urgent need to provide a disposable diaper having smaller wrinkles and pleats.

Japanese Unexamined Patent Application Publication No. 2002-238934, for example, provides a disposable diaper in which elastic threads for the body of disposable shorts are spaced 1 to 5 mm apart in a circumferential direction with the threads positioned between a front-side armored member and a back-side armored member in a body fit portion of disposable shorts and a vertically-long fine gather with a pitch of not more than approximately 3 mm is formed throughout the body fit portion.

DISCLOSURE OF THE INVENTION

Problems to be Solved by the Invention

However, in the above-mentioned configuration in which the elastic threads are spaced 1 to 5 mm apart in the circumferential direction so as to be positioned between the front-side armored member and the back-side armored member in a torso-surrounding stretchable portion, the weight per unit of an elastic member or adhesives increases. Therefore, there is no large and deep rib, so that a stiff feeling is eliminated. However, the rigidity is high. Therefore, a contact sensation in the skin may, in some cases, be reduced.

Alternatively, a method utilizing a stretchable nonwoven fabric is also taken as an example. However, stretchability is insufficient to employ the nonwoven fabric as a disposable diaper or the like, so that it may, in some cases, negative impact the cost.

The present invention has been made in view of the foregoing and an objective is to provide a sheet member that has flexible and small irregular wrinkles (concavities and convexities) and can be employed with adhesion to a user to improve the contact feeling, a disposable diaper using the sheet member, and a method of manufacturing a high-density region-containing sheet serving as a sheet composing the sheet member.

Means for Solving the Problems

The inventors of the present invention have conducted a thorough examination in order to solve the above-mentioned problem. As a result, they have discovered that a sheet member which has flexible and small irregular wrinkles (concavities and convexities) and provides a low level of skin stimulation by laminating two high-density region-containing sheets each having high-density regions alternating with low-density regions with an elastic member positioned therebetween, and have discovered a disposable diaper that has an increased adhesion to a user, reduced foreign-body sensation, and provides a low level of skin stimulation by employing an outer member having sheet members laminated therein for a chassis of the disposable diaper, to complete the present invention. More specifically, the present invention is characterized by the following.

According to a first aspect of the present invention, a sheet member is provided, including a first sheet, a second sheet, and at least one elastic member having a shape selected from a thread shape, a net shape, a strip shape, and a sheet shape, arranged between the first sheet and the second sheet, characterized in that the first sheet has a plurality of high-density regions and a plurality of low-density regions continuously formed therein such that the high-density regions substantially alternate with the low-density regions in a predetermined direction, the elastic member is arranged in the predetermined direction in which the plurality of high-density regions alternate with the plurality of low-density regions, and at least a part of each of the plurality of high-density regions is attached to the elastic member in an expanded state.

In a second aspect of the sheet member as described in the first aspect of the present invention, at least the first sheet is formed to have concavities and convexities, in the predetermined direction, in the sheet member.

In a third aspect of the sheet member as described in the first or second aspect of the present invention, the density of the high-density region is 0.05 to 0.6 g/cm$^3$ in the sheet member in order to obtain a first rigidity.

In a fourth aspect of the sheet member as described in any one of the first to third aspects of the present invention, the density of the low-density region is 0.01 to 0.05 g/cm³ in the sheet member in order to obtain a second rigidity.

In a fifth aspect of the sheet member as described in any one of the first to fourth aspects of the present invention, the length of the high-density region is 0.1 to 1.5 mm in the sheet member.

In a sixth aspect of the sheet member as described in any one of the first to fifth aspects of the present invention, the length of the low-density region is 0.5 to 3 mm in the sheet member.

In a seventh aspect of the sheet member as described in any one of the first to sixth aspects of the present invention, the elastic member is coated with an adhesive, and when attached to the first sheet and the second sheet of the sheet member, is more rigidly held to the high-density region than the low-density region.

In an eighth aspect of the sheet member as described in any one of the first to seventh aspects of the present invention, the following equation 1 is satisfied:

$$(A+C)/X \geq A \qquad \text{Equation 1}$$

wherein A is the length of the high-density region, C is the length of the low-density region, and X is the substantial expansion magnification of the elastic member.

According to a ninth aspect of the present invention, a high-density region-containing sheet manufacturing method is provided, including the step of compressing a sheet with shaping rolls, each having a toothed area, to manufacture a high-density region-containing sheet having a plurality of high-density regions and a plurality of low-density regions formed therein.

In a tenth aspect of the present invention, the high-density region-containing sheet manufacturing method as described in the ninth aspect is provided, in which the high-density region-containing sheet formed to have concavities and convexities in the longitudinal direction is manufactured.

In an eleventh aspect of the present invention, the high-density region-containing sheet manufacturing method as described in the ninth or tenth aspect is provided, in which the sheet is compressed between a pair of the shaping rolls that rotate in a direction opposite to each other.

In a twelfth aspect of the present invention, the high-density region-containing sheet manufacturing method as described in the ninth or eleventh aspect is provided, in which the high-density region and the low-density region alternate with each other in the longitudinal direction of the sheet.

In a thirteenth aspect of the present invention, the high-density region-containing sheet manufacturing method as described in the twelfth aspect is provided, in which one of the shaping rolls has at least one toothed area and at least one grooved area.

In a fourteenth aspect of the present invention, the high-density region-containing sheet manufacturing method as described in any one of the ninth to thirteenth aspects is provided, in which the method is characterized in that the grooved area may be covered with a thermally insulating material.

According to a fifteenth aspect of the present invention, a high-density region-containing sheet manufacturing method is provided, including the step of melting a low-density sheet, filming a part of the low-density sheet, and adding high-density regions to the sheet.

According to a sixteenth aspect of the present invention, a disposable diaper is provided, including a chassis composed of a front torso-surrounding portion and a rear torso-surrounding portion, and having a torso-surrounding opening and a pair of right and left leg-surrounding openings positioned in an under-crotch portion; a liquid-permeable top sheet disposed in at least a part of the chassis; a liquid-impermeable back sheet disposed on a first side in the thickness direction, of the liquid-permeable top sheet; and an absorbent core having liquid holding properties disposed between the liquid-permeable top sheet and the liquid-impermeable back sheet, the sheet member as described in any one of the first to eighth aspects of the present invention, is disposed in an area between the torso-surrounding opening and the leg-surrounding openings of the chassis.

Effects of the Invention

According to the present embodiment, a sheet member that can provide a wearer with satisfactory adhesion during wearing, and a disposable diaper using the sheet member can be provided.

PREFERRED MODE FOR CARRYING OUT THE INVENTION

The present invention is characterized by compressing a sheet using shaping rolls each having a toothed area, to manufacture a high-density region-containing sheet having high-density regions and low-density regions. Further, the present invention is characterized in that the high-density region-containing sheet has flexible and irregular small pleats formed therein by attaching the high-density regions of the high-density region-containing sheet to an elastic member in an expanded state, and is characterized in that the high-density region-containing sheet is employed as a chassis for a disposable diaper. Although embodiments of a high-density region-containing sheet manufacturing method, a sheet member, and a disposable diaper according to the present invention will be described in detail, the present invention is not limited to the following embodiments but can be carried out by making changes, as needed, within the scope of the present invention. Although a description may, in some cases, be omitted, this does not necessarily limit the spirit of the present invention.

High-Density Region-Containing Sheet Manufacturing Method

Figure 1:
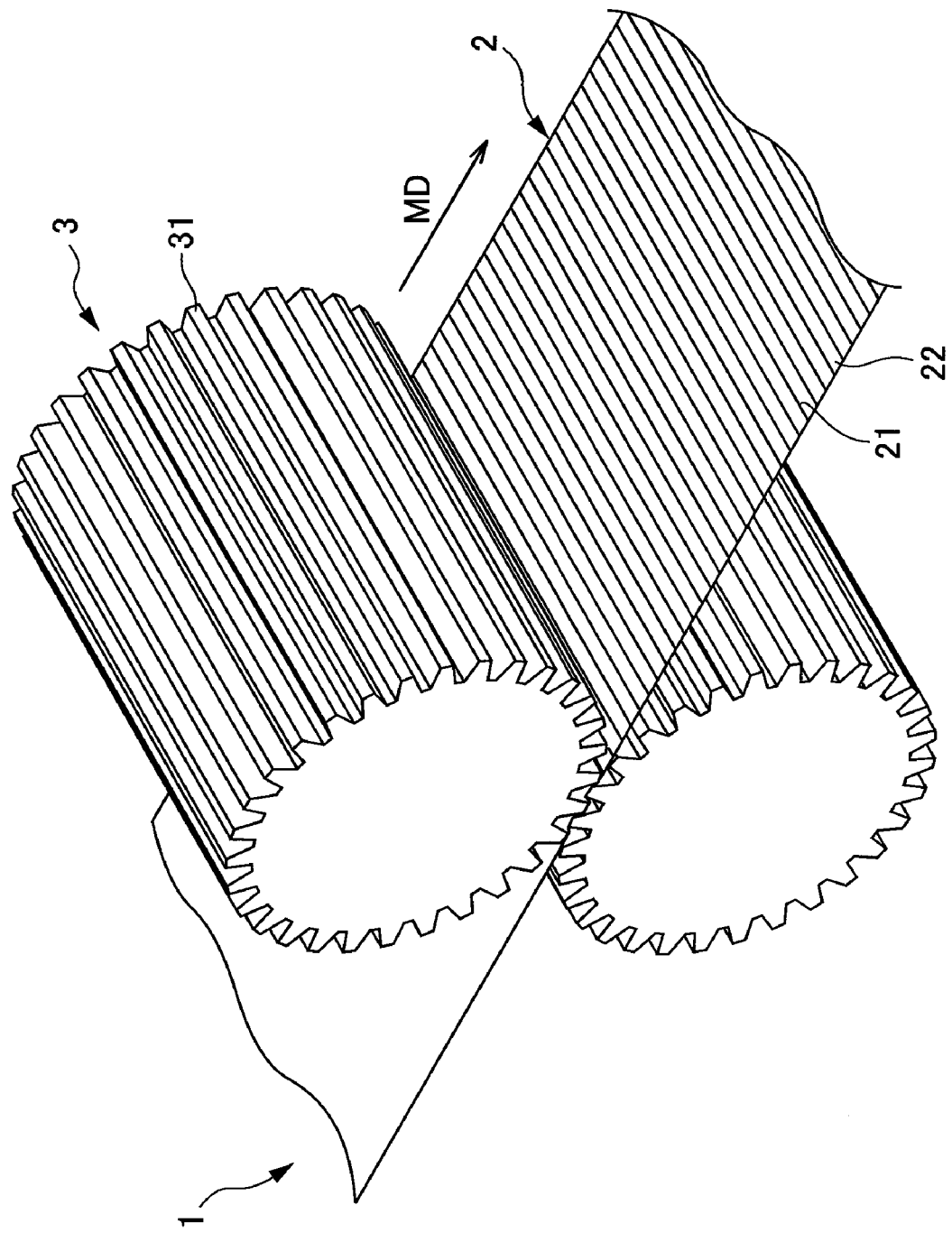
FIG. 1 is a diagram showing a high-density region-containing sheet manufacturing method according to the present invention.
Figure 4:
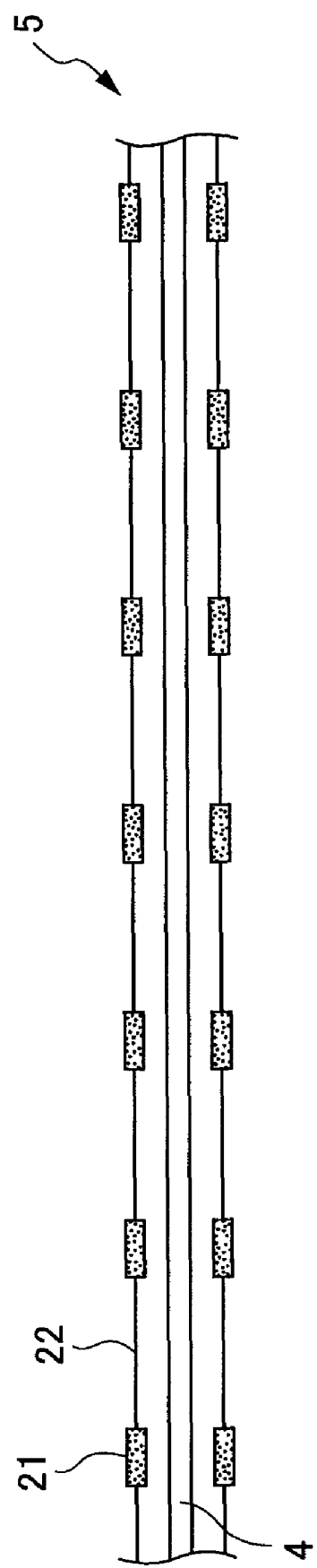
FIG. 4 is a cross-sectional view of a planar high-density region-containing sheet.

FIG. 1 is a diagram showing an example of a high-density region-containing sheet manufacturing method according to the present invention. A sheet 1 is compressed using a pair of shaping rolls 3 each composed of an embossing roll or the like as shown in FIG. 1, and the sheet 1 having a high density is previously expanded to provide low-density regions 22, thereby manufacturing a high-density region-containing sheet 2. The shaping roll 3 has toothed areas 31 each having a plurality of teeth of a predetermined size. The paired shaping rolls 3 rotate in a direction opposite to each other, to compress the sheet 1. The portion which has been compressed by the teeth of the toothed area 31, of the sheet 1, serves as a low-density region 22 by expansion of fibers, and the portion thereof which has not been compressed serves as a high-density region 21. When the sheet 1 passes between the rotating paired shaping rolls 3, an area which has been compressed by the teethed area 31 has the high-density regions 21 and the low-density regions 22 formed therein for each clearance between the teeth, as shown in FIG. 4. Although the sheet 1 is compressed by the pair of shaping rolls 3 in FIG. 1, the sheet 1 may be compressed using only one of the shaping rolls 3 when the sheet 1 has a high density.

The high-density regions 21 alternate with the low-density regions 22 for each clearance between the teeth of the toothed area 31, that is, in a longitudinal direction of the sheet 1, i.e., a machine direction (MD) of the sheet 1 on which the shaping rolls 3 are passed. Although the length of the low-density region 22 (the distance between the high-density region 21 and the nearest high-density region 21 and the width of the teeth of the toothed area 31) can be modified, as needed, in accordance with the intended use or the like of the high-density region-containing sheet 2 to be obtained, it is preferably 0.5 to 3 mm. When the length of the low-density region 22 is less than 0.5 mm, a sheet member having flexible and small irregular wrinkles (concavities and convexies) formed therein and providing a low degree of skin stimulation, the details of which are described later, cannot be provided. Alternatively, when the length of the low-density region 22 exceeds 3 mm, a sheet member having flexible and small irregular wrinkles (concavities and convexities) formed therein and providing a low degree of skin stimulation, the details of which are described later, cannot be provided.

Although the length of the high-density region 21 can be modified, as needed, in accordance with the intended use or the like of the high-density region-containing sheet 2 to be manufactured, it is preferably 0.1 to 1.5 mm. When the length of the high-density region 21 is less than 0.1 mm, a sheet member having flexible and small irregular wrinkles (concavities and convexities) formed therein and providing a low degree of skin stimulation, the details of which are described later, cannot be provided. Alternatively, when the length of the high-density region 21 exceeds 1.5 mm, a sheet member having flexible and small irregular wrinkles (concavities and convexities) formed therein and providing a low degree of skin stimulation, the details of which are described later, cannot be provided.

Although the rigidity of the low-density region 22 can be modified, as needed, in accordance with the intended use or the like, the density obtaining a predetermined rigidity is preferably 0.01 to 0.05 g/cm$^3$. When the density of the low-density region 22 is less than 0.01 g/cm$^3$, a sheet member having flexible and small irregular wrinkles (concavities and convexities) formed therein and providing a low degree of skin stimulation, the details of which will be described later, cannot be provided because it too much contracts because of the elastic member. Alternatively, when the density of the low-density region 22 exceeds 0.05 g/cm$^3$, a sheet member having flexible and small irregular wrinkles (concavities and convexities) formed therein and providing a low degree of skin stimulation, the details of which are described later, cannot be provided because the rigidity thereof becomes too high.

It is preferable that the density of the sheet 1, is 0.05 to 0.6 g/cm$^3$ in order to obtain a predetermined rigidity of the high-density region 21. When the density of the high-density region 21 is less than 0.05 g/cm$^3$, a sheet member having flexible and small irregular wrinkles (concavities and convexities) formed therein and providing a low degree of, the details of which are described later, cannot be provided because the rigidity thereof is approximately the same as that of the low-density region 22. Alternatively, when the density of the high-density region 21 exceeds 0.6 g/cm$^3$, a sheet member having flexible and small irregular wrinkles (concavities and convexities) formed therein and providing a low degree of skin stimulation, the details of which are described later, cannot be provided because the rigidity thereof becomes too high.

Examples of a nonwoven fabric used for the sheet 1 include various types of known nonwoven fabrics such as a spunbonded nonwoven fabric, a meltblown nonwoven fabric, a heat roll nonwoven fabric, an SMS nonwoven fabric which is a combination of a spunbonded nonwoven fabric and a meltblown nonwoven fabric, an air-through nonwoven fabric, a spun lace nonwoven fabric, and an airlaid nonwoven fabric, which can be changed, as needed, in accordance with the intended use or the like. The nonwoven fabrics may be employed alone or in combination. In order to form flexible wrinkles that are pleasant to the eye and are nice to the touch, it is more preferable to use an air-through nonwoven fabric, a heat roll nonwoven fabric, a spun lace nonwoven fabric, a spunbonded nonwoven fabric, and a meltblown nonwoven fabric.

Although a material for fibers composing the nonwoven fabric used for the sheet 1 can be changed, as needed, in accordance with the intended use or the like, examples of the material include various types of known fibers such as polyethylene, polypropylene, polyester, and acryl, conjugate fibers such as polyethylene/polypropylene, polyethylene/polyethylene terephthalate, and polypropylene/polyethylene terephthalate, i.e., fibers formed of core-in-sheath fibers and side-by-side fibers. The fibers may be used alone or in combination. Further, the sheet 1 may have a monolayer structure or a multilayer structure.

The basis weight of the nonwoven fabric used for the sheet 1 is preferably 5 to 50 g/m$^2$ and more preferably 10 to 20 g/m$^2$. If the basis weight of the nonwoven fabric is less than 5 g/m$^2$, a portion where the strength is reduced because of marked nonuniformity may appear and tear. Alternatively, when the basis weight of the nonwoven fabric exceeds 20 g/m$^2$, air permeability is retarded, and the inside of the disposable diaper may become stuffy when worn for an extended period.

The elongation percentage of the nonwoven fabric used for the sheet 1 is not particularly limited, provided that it is not less than 40%. When the elongation percentage of the nonwoven fabric is less than 40%, the nonwoven fabric may break in forming flexible and small irregular wrinkles (concavities and convexities).

Figure 2:
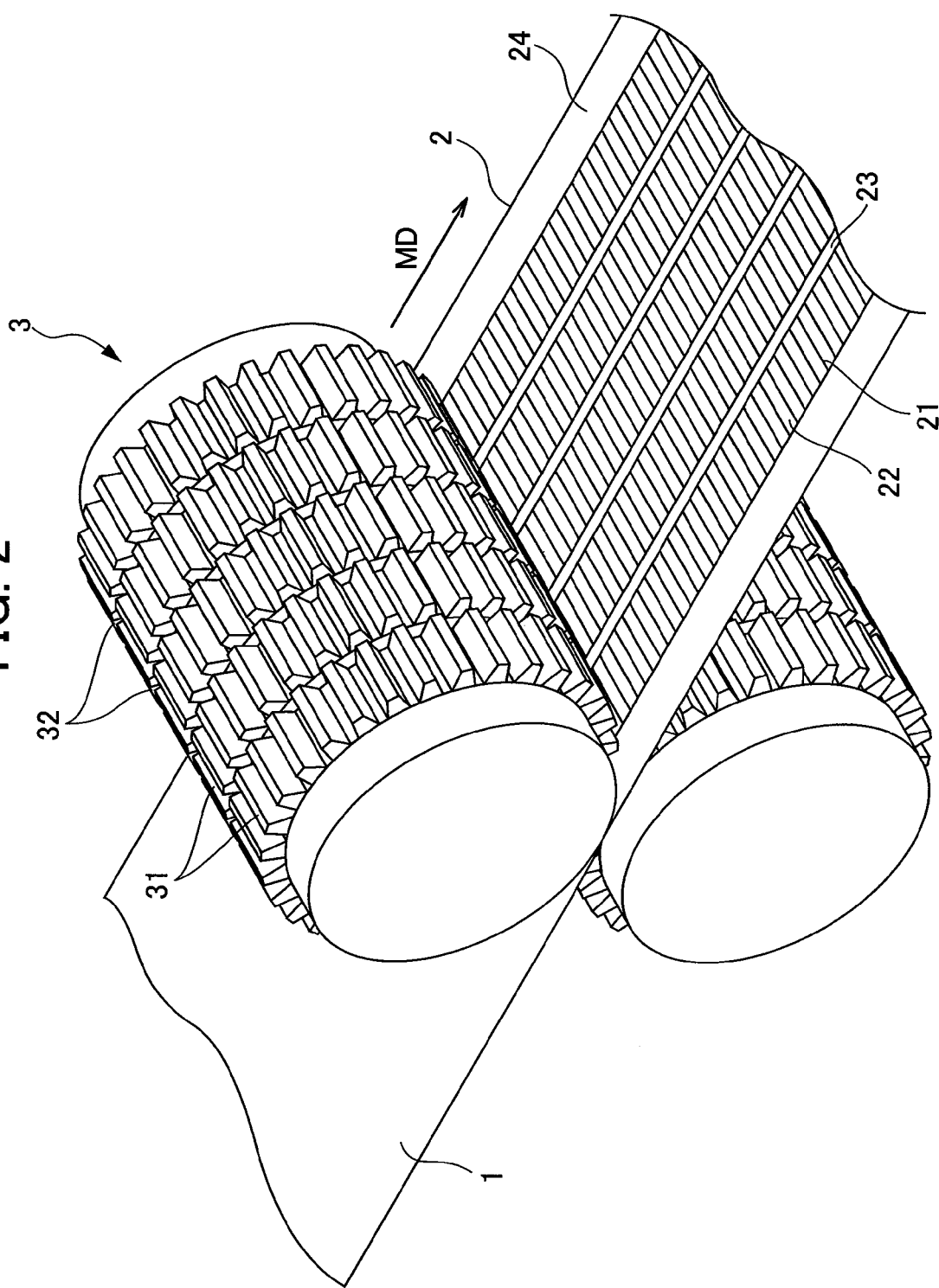
FIG. 2 is a diagram showing another example of a high-density region-containing sheet manufacturing method according to the present invention.
Figure 3:
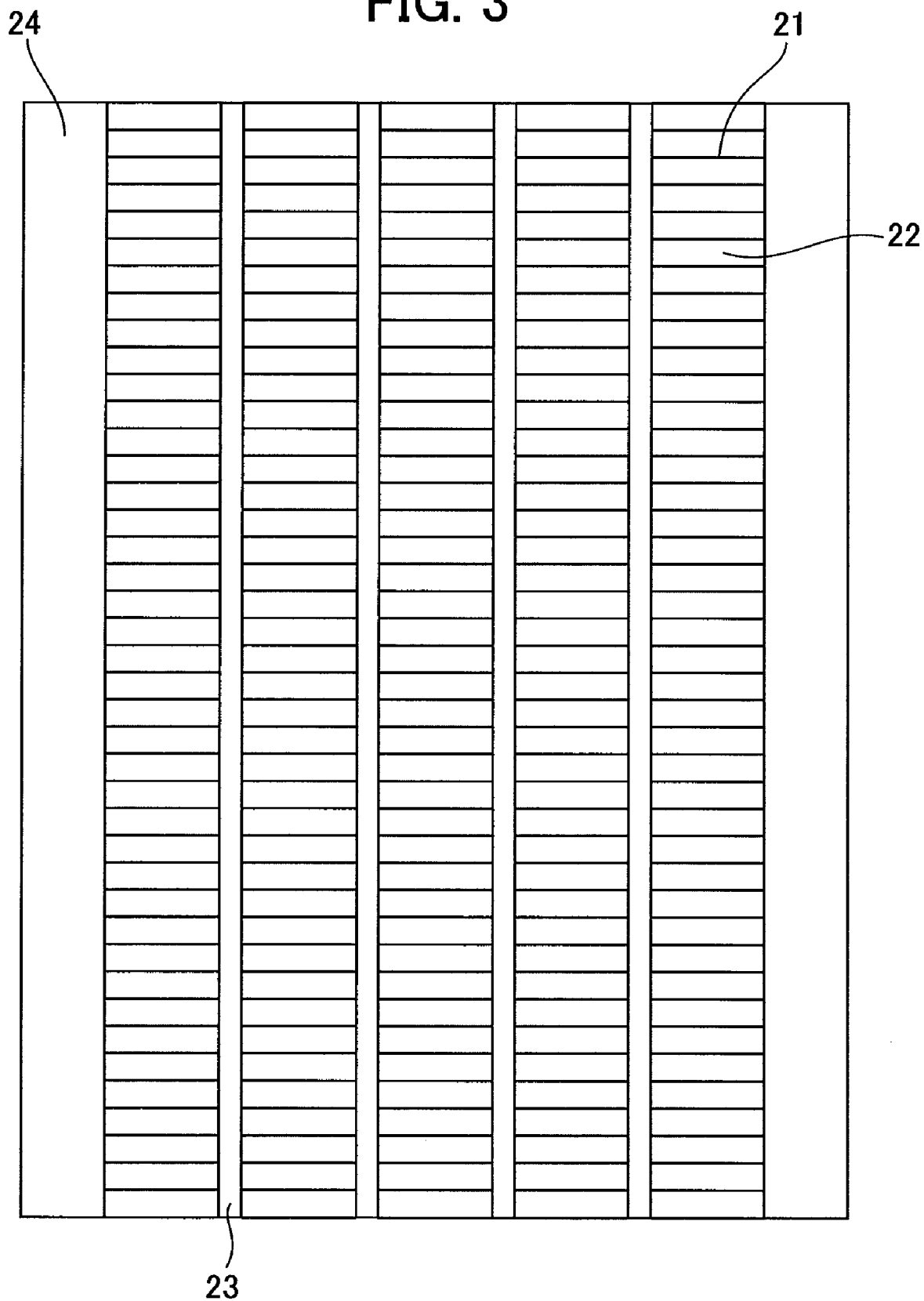
FIG. 3 is a plan view of a high-density region-containing sheet obtained by the example shown in FIG. 2.

The high-density region-containing sheet can be manufactured as shown in FIG. 2, for example, in addition to the manufacturing method shown in FIG. 1. The example shown in FIG. 2 differs from the example shown in FIG. 1 in that each of a pair of shaping rolls 3 has toothed areas 31 each having a plurality of teeth of a predetermined size and planar grooved areas 32 each having no teeth, and has the toothed areas 31 alternating with the grooved areas 32. When the sheet 1 is passed between the rotating paired shaping rolls 3, areas, which have been respectively compressed by the teethed areas 31, of the sheet 1 respectively form low-density regions 22 by expanding the sheet 1. Therefore, a high-density region-containing sheet 2 having an area (a shaped area) having high-density regions 21 and low-density regions 22 formed therein and an area (a groove area 23) that is not shaped by the grooved areas 32 can be obtained, as shown in FIG. 3. The high-density region-containing sheet 2 may have an adhesive layer 24 to be joined to other members, as needed.

Although the width of the toothed area 31 shown in FIG. 2 can be modified, as needed, in accordance with the intended use or the like of the high-density region-containing sheet 2 to be manufactured, it is preferable that the width is 2 mm to 10 cm and more preferably 3 to 9 mm. When the width of the toothed area 31 is less than 2 mm, projections of flexible and small irregular wrinkles (concavities and convexities) of the sheet member, the details of which are described later, are crushed, so that the shape of the flexible and small irregular wrinkles (concavities and convexities) cannot be held. Alternatively, when the width of the toothed area 31 exceeds 10 cm, the sheet member expands, so that the shape of the flexible and small irregular wrinkles (concavities and convexities) cannot be held.

Although the width of the grooved area 32 shown in FIG. 2 can be modified, as needed, in accordance with the intended use or the like of the high-density region-containing sheet 2 to be manufactured, it is preferable that the width is 0.5 mm to 3 cm and more preferably 1 to 5 mm. When the width of the grooved area 32 is less than 0.5 mm, projections of the sheet member, the details of which are described later, may be crushed, so that flexible and small irregular wrinkles (concavities and convexities) cannot be formed. Alternatively, when the width of the grooved area 32 exceeds 3 cm, the ratio of the groove area 23, having no flexible and small irregular wrinkles (concavities and convexities), to the whole high-density region-containing sheet 2 is increased.

In the shaping roll 3, the grooved areas 32 are covered with a thermally insulating material such as a heat insulation tape such that heat is not transmitted to an area other than the toothed areas 31. Heat is applied to only an area, to be shaped, of the sheet 1, which allows damage to the high-density region-containing sheet 2 to be minimized. Therefore, deformation such as a decrease in width and twisting of the high-density region-containing sheet 2 can be prevented.

After passing between the shaping rolls 3, the sheet 1 may be cooled, as needed, in order to hold the molding of the shaped high-density regions 21 of the manufactured high-density region-containing sheet 2.

The manufacturing method disclosed in FIGS. 1 and 2 include a mesh plate, embossing, thermoforming, high-pressure hydroforming, injection molding, and so on. In addition to the manufacturing method described in FIGS. 1 and 2, when a low-density nonwoven fabric such as an air-through nonwoven fabric is used, for example, a method of adding high-density regions 21 to the nonwoven fabric by melting the nonwoven fabric once using heat treatment, ultrasonic treatment, or the like and filming the nonwoven fabric may be used. In this case, heat-treated portions respectively form the high-density regions 21, and untreated portions respectively form the low-density regions 22. Further, the high-density regions 21 may be formed by a line-shaped or dot-shaped set using embossing, for example.

According to the high-density region-containing sheet manufacturing method in the present embodiment, deformation such as a decrease in width and twisting of a material can be prevented. Therefore, the high-density region-containing sheet 2 having the high-density regions 21 alternating with the low-density regions 22 can be efficiently manufactured. As the high-density region-containing sheet 2 obtained by the embodiment, both a planar sheet and a sheet in which each of high-density regions 21 and low-density regions 22 has flexible and small irregular wrinkles (concavities and convexities) continuously formed therein such that projections alternate with recesses in a longitudinal direction or machine direction (MD) can be obtained depending on the difference in pressure for compressing the sheet 1, and can be used separately, as needed, in accordance with the intended use or the like.

Sheet Member

The high-density region-containing sheet 2 obtained by the manufacturing method described in FIG. 1 or FIG. 2, for example, has high-density regions 21 alternating with low-density regions 22, as shown in FIG. 4. A sheet member 5 can be obtained by attaching the high-density region-containing sheet 2 (a first sheet or a second sheet) to an elastic member 4 in an expanded state. The sheet may be the high-density region-containing sheet 2. A sheet member 5 obtained by attaching two high-density region-containing sheets 2 to an elastic member 4 will be now described for convenience of illustration.

Figure 5:
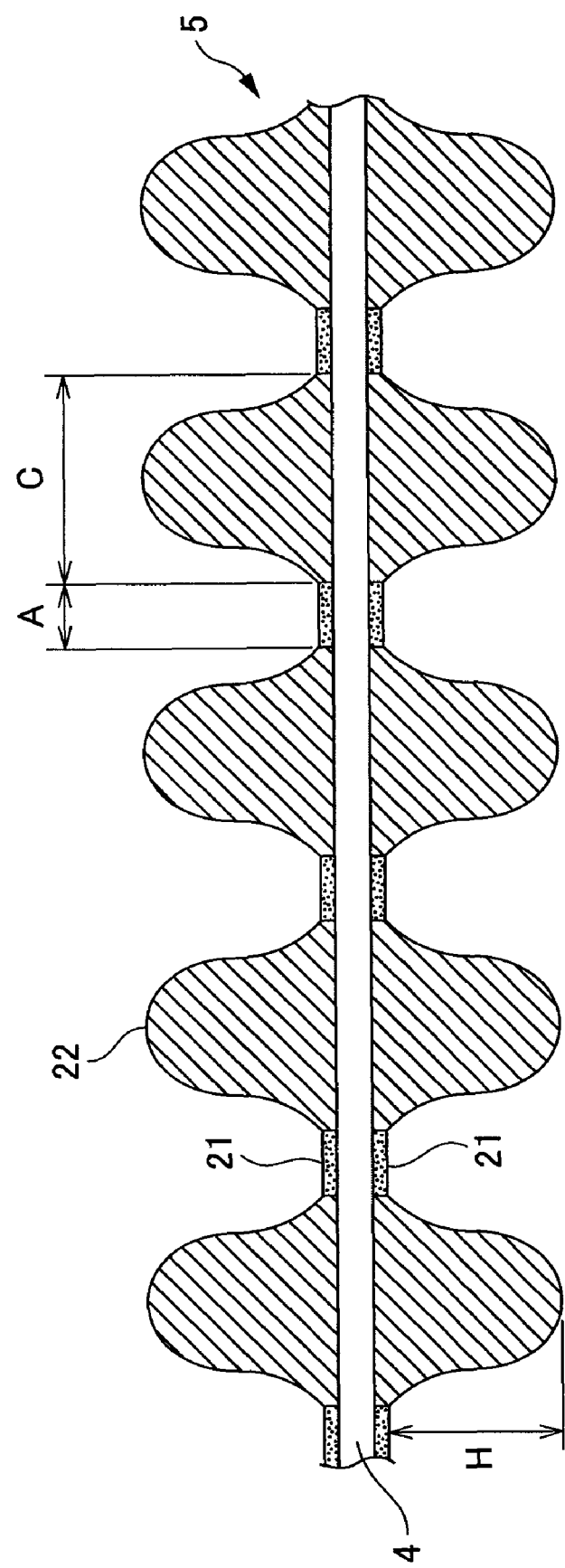
FIG. 5 is a cross-sectional view of a sheet member according to the present invention.

FIG. 5 is a cross-sectional view of the sheet member 5 obtained by attaching the two high-density region-containing sheets 2 to the elastic member 4. The two high-density region-containing sheets 2 are joined to each other with the elastic member 4 sandwiched therebetween. When the high-density region-containing sheet 2 is joined to the elastic member 4, an adhesive is directly applied to the elastic member 4, to join the high-density region-containing sheets 2 with the expanded elastic member 4. Since low-density regions 22 are immediately stripped because the fiber density thereof is low even if the elastic member 4 is made to adhere thereto, only high-density regions 21 are attached to the elastic member 4. Consequently, the elastic member 4 and only the high-density regions 21 are attached to each other, as shown in FIG. 5. When the elastic member 4 contracts, the low-density regions 22 also contract, so that flexible and small irregular wrinkles (concavities and convexities) are formed therein.

Consider a case where the high-density region-containing sheet 2 is present in a planar form. A is defined as the length of the high-density region 21, C is defined as the length of the low-density region 22, and X is defined as the substantial magnification of the elastic member 4, pleats are formed only when the following equation 1 is satisfied. Unless the equation 1 is satisfied, no pleats can be formed because the low-density regions 22 do not regularly contract even if the elastic member 4 in the sheet member 5 contracts.

$$(A+C)/X \geqq A \qquad \text{Equation 1}$$

In a case where the high-density region-containing sheet 2 has an irregular (concavo-convex) shape and has an irregular pattern continuously formed therein, pleats are similarly formed only when equation 1 is satisfied. Unless equation 1 is satisfied, pleats cannot be formed because the low-density regions 22 do not regularly contract even if the elastic member 4 in the sheet member 5 contracts.

Although the coating amount of adhesive to be directly applied to the elastic member 4 can be modified, as needed, in accordance with the property or the like of the high-density region-containing sheet 2 or the like, it is preferable that the coating amount is 0.02 to 0.2 g/m². If the coating amount is less than 0.02 g/m², the high-density regions 21 and the elastic member 4 cannot be attached to each other. Alternatively, when the coating amount exceeds 0.2 g/m², the low-density regions 22 are also attached to the elastic member 4, so that pleats cannot be formed.

Although the method of attaching the elastic member 4 and the high-density regions 21 to each other can be changed, as needed, in accordance with the intended use or the like of the sheet member 5, it is preferable that the elastic member 4 is fixed to the high-density regions 21 by a coating method in which the elastic member 4 can be directly coated, for example, V-slit coating, Ω coating, or control seam coating from the viewpoint of making it easy to form uniform projections 51 without inhibiting the low-density regions 22 themselves from contracting and eliminating the necessity of aligning the coating position of adhesives with the elastic member 4.

Figure 6:
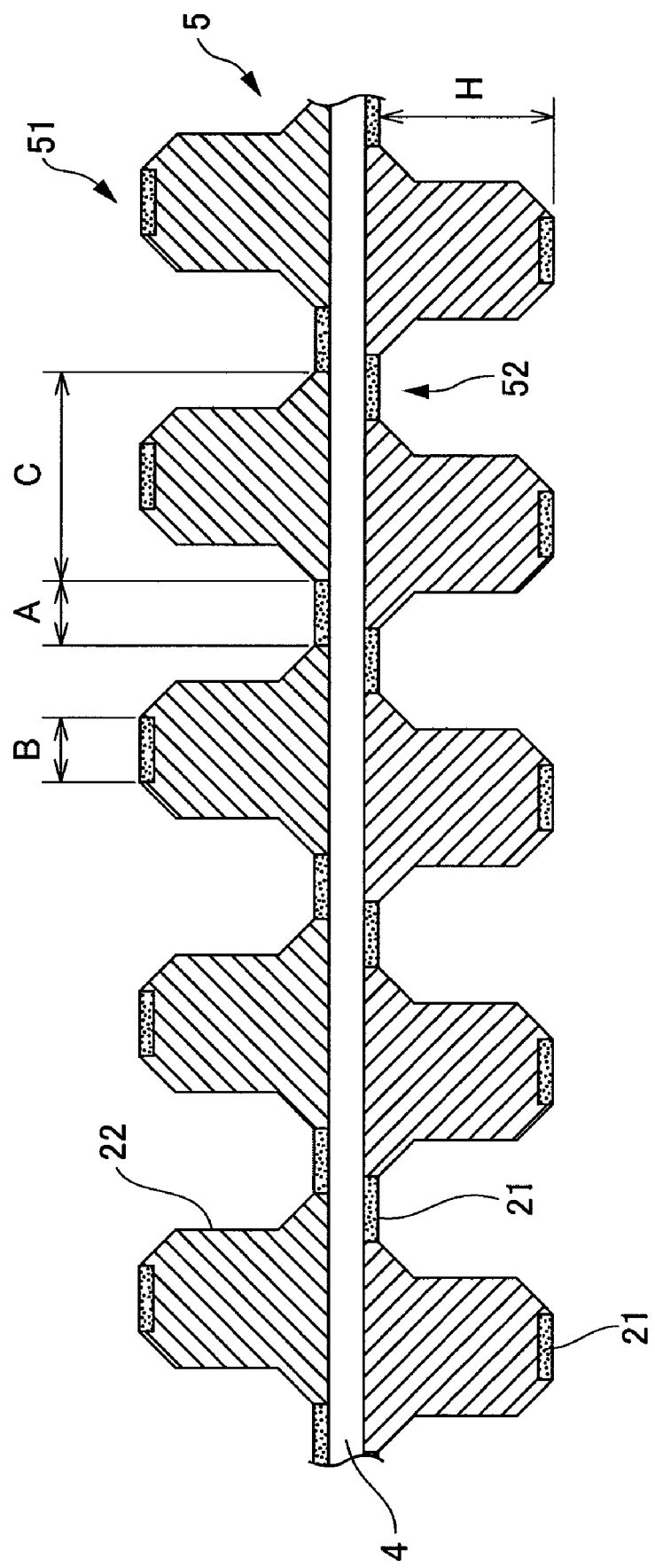
FIG. 6 is a cross-sectional view of another example of the sheet member according to the present invention.

As shown in FIG. 6, the alternate high-density regions 21 out of the plurality of high-density regions 21 may be attached to the elastic member 4 in an expanded state. The high-density region-containing sheet 2 on the top of the elastic member 4 shown in FIG. 5 is hereinafter referred to as a front-surface high-density region-containing sheet, and the high-density region-containing sheet 2 on the bottom of the elastic member 4 is hereinafter referred to as a back-surface high-density region-containing sheet for convenience of illustration. By attaching the alternate high-density regions 21 to the elastic member 4 in an expanded state, the high-density regions 21 that are not attached to the elastic member 4 separate from the elastic member 4 when the elastic member 4 contracts, so that flexible and small irregular wrinkles (concavities and convexities) are formed therein, as shown in FIG. 6. The top of the projection 51 and the bottom of the recess 52 in the flexible and small irregular wrinkles (concavities and convexities) are formed by the high-density region 21, and a portion between the top of the projection 51 and the bottom of the recess 52 is formed by the low-density region 22. The high-density regions 21 do not contract because the rigidity thereof is high even if the elastic member 4 contracts, and only the low-density regions 22 contract, which allows a sheet member 5 having a regularly irregular pattern to be obtained. Further, the low-density region 22 is formed between the top of the projection 51 and the bottom of the recess 52, which allows a sheet member 5 having flexible and small irregular wrinkles (concavities and convexities) formed therein and providing a low degree of skin stimulation to be obtained. Only the low-density regions 22 contract when conditions expressed by the foregoing equation 1 are satisfied, as in a case where all the high-density regions 21 are joined to the elastic member 4. In this case, in equation 1, A is the length of the high-density region 21 at the bottom of the recess 52, C is the contractibility of the low-density region 22, and X is the substantial expansion rate of the elastic member 4.

The height H of the projection 51 is approximately the same as the length of the low-density region 22 (the distance between the high-density region 21 and the nearest high-density region 21 and the width of the teeth of the toothed area 31). Although the height H of the projection 51 can be modified, as needed, in accordance with the intended use or the like of the sheet member 5, it is preferably 0.5 to 3 mm. When the height H of the projection 51 is less than 0.5 mm, a sheet member having flexible and small irregular wrinkles (concavities and convexities) formed therein and providing a low degree of skin stimulation cannot be provided. Alternatively, when the height H of the projection 51 exceeds 3 mm, the adhesion to a user, who is wearing an item that includes the sheet member 5, is reduced.

Furthermore, the length B at the top of the projection 51 and the length A at the bottom of the recess 52 are the same as the length of the high-density region 21. Although the length A at the bottom and the length B at the top can be modified, as needed, in accordance with the intended use or the like of the sheet member 5 as described above, they are preferably 0.1 to 1.5 mm. When the lengths A and B are less than 0.1 mm, a sheet member having flexible and small irregular wrinkles (concavities and convexities) formed therein and providing a low degree of skin stimulation cannot be provided. Alternatively, when the lengths A and B exceed 1.5 mm, the contact area with the high-density region 21 increases, and when the user wears an item including the sheet member 5, the tactile sensation of the item becomes hard and is unpleasant.

Although the respective heights H of the irregular pattern on the front surface and the back surface of the sheet member 5 shown in FIGS. 5 and 6 are the same, a sheet member 5 in which the respective heights H of an irregular pattern on the front surface and back surface differ, the respective lengths A at the bottom of recesses of the irregular pattern differ, and the respective lengths B at the top of projections of the irregular pattern differ, for example, can be obtained by attaching a high-density region-containing sheet 2 the high-density regions 21 and/or low density regions 22 respectively have different widths or the like to an elastic member 4.

Although the form of the elastic member 4 is not particularly limited and can be modified, as needed, in accordance with the intended use or the like, examples of the form include a strip shape, a sheet shape, a net shape, and a thread shape. The sheet member 5 may be configured in a single form. Alternatively, the sheet member 5 may be configured in a plurality of forms.

Although a pitch with which the elastic member 4 is interposed can be modified, as needed, in accordance with the intended use or the like of the sheet member 5, it is preferably 1 to 30 mm and more preferably 6 to 8.5 mm. When the user wears an item including the sheet member 5 and the pitch is less than 1 mm, the linear pressure increases resulting in a rubber track pressure mark track being left on the user's skin. Alternatively, when the users wears an item including the sheet member 5, and the pitch exceeds 30 mm, the sheet member 5 is not affected by the elastic member 4, resulting in a decreased surface pressure on the user so that the item slips.

Although the size of the elastic member 4 can be modified, as needed, in accordance with the intended use or the like of the sheet member 5, it is preferably 310 to 1440 deniers and more preferably 420 to 940 deniers. When the size of the elastic member 4 is less than 310 deniers, the number of elastic members 4 must be increased in order to create a stress to increase the magnification of the elastic member 4. Therefore, the linear pressure increases, which causes a rubber track pressure mark to be made on the user when the user wears the item including the sheet member 5. In addition, when the size of the elastic member 4 exceeds 1440 deniers, the linear pressure increases, which causes a rubber track pressure mark to be made on the user when the user wears the item including the sheet member 5.

Although a material for the elastic member 4 can be modified, as needed, in accordance with the intended use or the like of the sheet member 5, examples of the material include various types of known materials, for example, synthetic rubber such as styrene-butadiene, butadiene, isoprene, and neoprene, natural rubber, EVA (ethylene vinyl acetate), SIS (styrene-isoprene-styrene), SEBS (styrene-ethylene butylene-styrene), SEPS (styrene-ethylene propylene-styrene), stretchable polyolefin, and polyurethane. These materials may be used alone or in combination.

Although the expansion rate (substantial expansion rate) of the elastic member 4 can be modified, as needed, in accordance with the intended use or the like of the sheet member 5, it is preferably 1.5 to 5 times, and more preferably 1.5 to 3.0 times. If the expansion magnification is less than 1.5 times, a regularly irregular pattern cannot be obtained even if the elastic member 4 contracts. Alternatively, when the expansion magnification exceeds 5.0 times, the sheet member 5 contracts even if the low-density regions 22 have completely contracted. Therefore, the whole sheet member 5 contracts, which causes large wrinkles and pleats to appear.

In the sheet member 5 according to the present embodiment, the elastic member 4 in an expanded state and the high-density regions 21 of the high-density region-containing sheet 2 are attached to each other. When the elastic member 4 contracts, therefore, the high-density regions 21 do not contract because the rigidity thereof is high, and only the low-density regions 22 contract. The results have allowed a stretchable nonwoven fabric having regular pleats to be obtained.

Disposable Diaper

Although a disposable diaper using the above-mentioned sheet member 5 will be described in detail below, a surface, directed toward the body of a user, of the disposable diaper is termed a skin touch surface, and a surface on the opposite side to the skin touch surface is termed a non-skin touch surface.

Figure 7A:
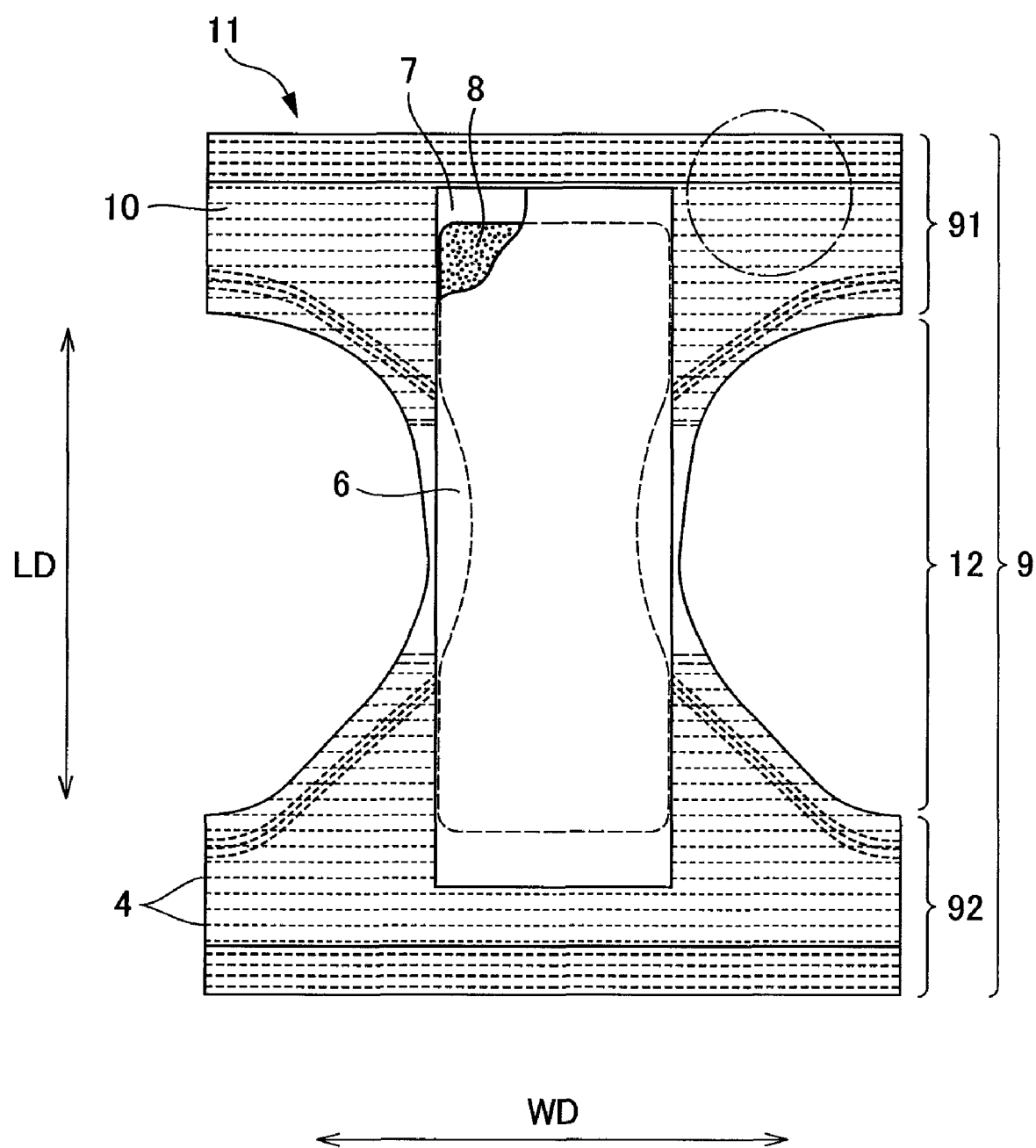
FIG. 7A is a front view of a disposable diaper using the sheet member according to the present invention.

FIG. 7A is a front view of the disposable diaper according to the present invention. As shown in FIG. 7A, the main body of the disposable diaper has a chassis 9 forming the outer shape of the disposable diaper body and composed of a front torso-surrounding portion 91 and a rear torso-surrounding portion 92 that are formed in the shape of shorts at the time of wearing, a liquid-permeable top sheet 6 provided on a surface, on the side of the skin touch surface, of the chassis 9 and formed in a substantially vertically-long shape composing a front surface layer, a liquid-impermeable back sheet 7 provided on a surface, on the side of the non-skin touch surface, of the chassis 9 on one side of the liquid-permeable top sheet 6 and formed in a substantially vertically-long shape composing a back surface layer, and an absorbent core 8 having liquid holding properties arranged between the liquid-permeable top sheet 6 and the liquid-impermeable back sheet 7, i.e., between the liquid-permeable top sheet 6 and the chassis 9 and formed in a substantially vertically-long shape composing an absorbing layer. Here, "vertically-long shape" shall include a substantially rectangular shape having a longitudinal direction LD and a shorter-side direction, i.e., a width direction WD, and shall include a shape both sides of which, in the longitudinal direction LD, are partially recessed in a direction toward the center in the longitudinal direction LD or raised in the opposite direction to the direction toward the center. That is, it is assumed that a part in the longitudinal direction LD of the absorbent core 8 differs in length in the width direction WD. Further, the absorbent core 8 may be arranged so as to be vertically-long in the width direction WD, or may be arranged so as to be vertically-long in the vertical direction.

The absorbent core 8 may be arranged in a state where it is wrapped in a tissue (not shown) or a hydrophilic nonwoven fabric (not shown). When wrapped in the hydrophilic nonwoven fabric, the absorbent core 8 may not use the liquid-permeable top sheet 6 or may only partially use the liquid-permeable top sheet 6. This allows the production cost to be reduced, for example. Further, a nonwoven fabric or the like may be joined to a surface, on the side of the non-skin touch surface, of the liquid-impermeable back sheet 7, which is preferable because the feel at the time of wearing by a user, for example, is improved. Further, when a film is used for the liquid-impermeable back sheet 7, a nonwoven fabric or the like may be joined to the film, which is preferable because an uncomfortable sound can be prevented from being produced by friction of the film, for example.

The chassis 9 has the front torso-surrounding portion 91 and the rear torso-surrounding portion 92 at the time of wearing, and an under-crotch portion 93 formed between the front torso-surrounding portion 91 and the rear torso-surrounding portion 92. The chassis 9 is formed in the shape of shorts by joining the front torso-surrounding portion 91 and the rear torso-surrounding portion 92 to each other at a joint 10 between predetermined positions of the front torso-surrounding portion 91 and the rear torso-surrounding portion 92. That is, the chassis 9 has a torso-surrounding opening 11 positioned around the abdomen of the user in a wearing state and a pair of leg-surrounding openings 12 respectively positioned around both legs of the user. Here, the predetermined positions of the front torso-surrounding portion 91 and the rear torso-surrounding portion 92 respectively refers to portions, excluding the leg-surrounding openings 12, of both ends of the front torso-surrounding portion 91 and the rear torso-surrounding portion 92 in a direction perpendicular to the vertical direction in the wearing state (hereinafter referred to as the width direction WD). The front torso-surrounding portion 91 and the rear torso-surrounding portion 92 also include portions distinguished by a center line in the width direction WD for dividing the longitudinal direction LD of the disposable diaper body into two, for example.

Figure 7B:
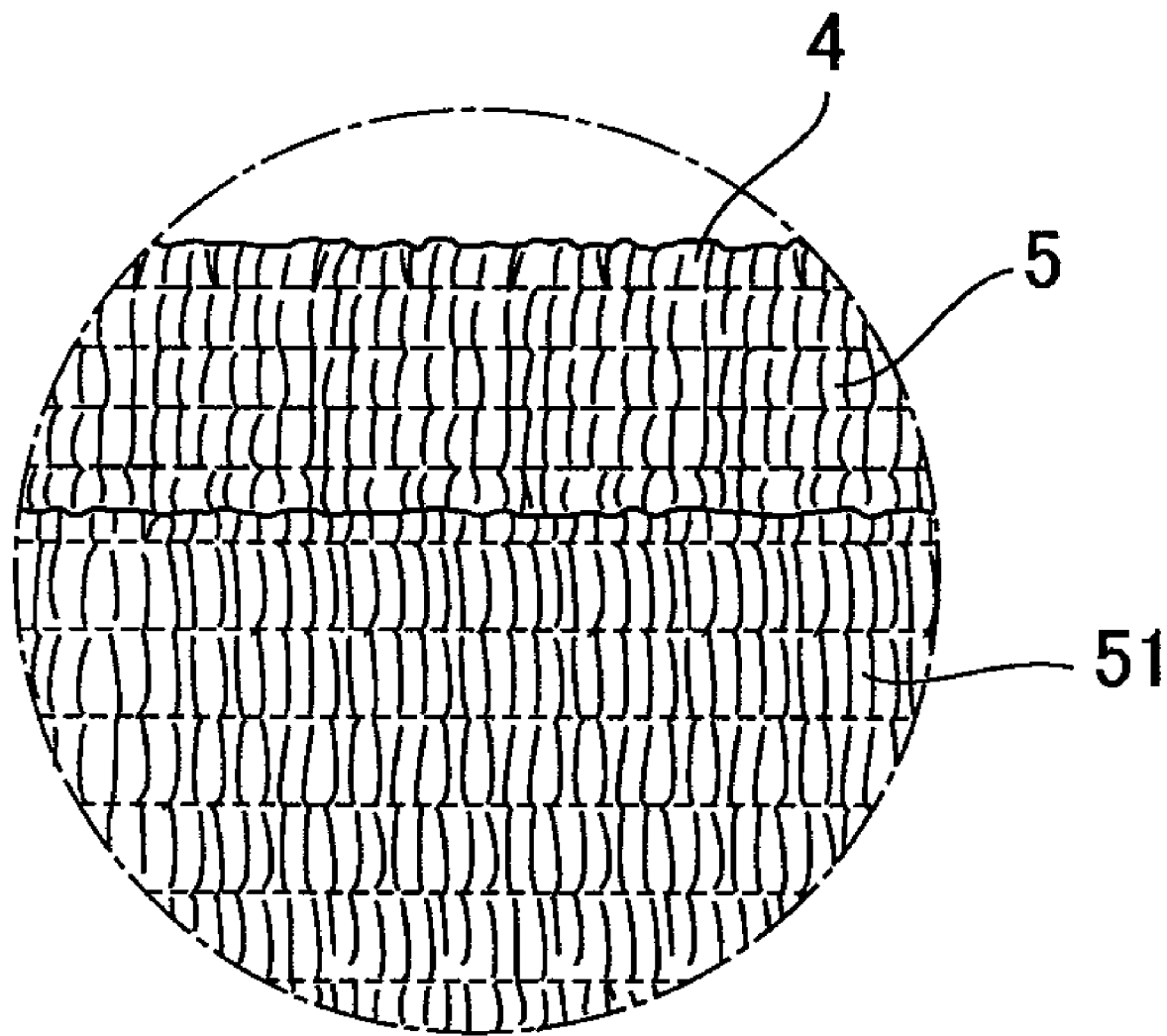
FIG. 7B is a partially enlarged view of a front torso-surrounding portion according to the present invention.

FIG. 7B is a partially enlarged view of the front torso-surrounding portion 91. The front torso-surrounding portion 91 is composed of the above-mentioned sheet member 5. When the elastic member 4 contracts by joining the two high-density region-containing sheets 2 each having the high-density regions 21 and the low-density regions 22 to each other with the elastic member 4 expanded, flexible and small irregular wrinkles (concavities and convexities), i.e., pleats are formed. In the sheet member 5, the high-density region-containing sheet 2 has an irregular pattern continuously formed therein such that projections alternate with recesses in a direction parallel to the torso-surrounding opening 1, and the elastic member 4 is also arranged along the projections and the recesses of the high-density region-containing sheet 2. Further, the sheet member 5 is arranged throughout an area between the torso-surrounding opening 11 and the pair of leg-surrounding openings 12. The rear torso-surrounding portion 92 also has an irregular pattern having a plurality of projections and recesses formed therein, similarly to the front torso-surrounding portion 91, because it is also composed of the sheet member 5, which is not illustrated. The irregular pattern extends in a direction substantially perpendicular to the longitudinal direction and extends in a substantially linear shape in the longitudinal direction. Further, the projections and the recesses are almost equally spaced around the torso.

Figure 8:
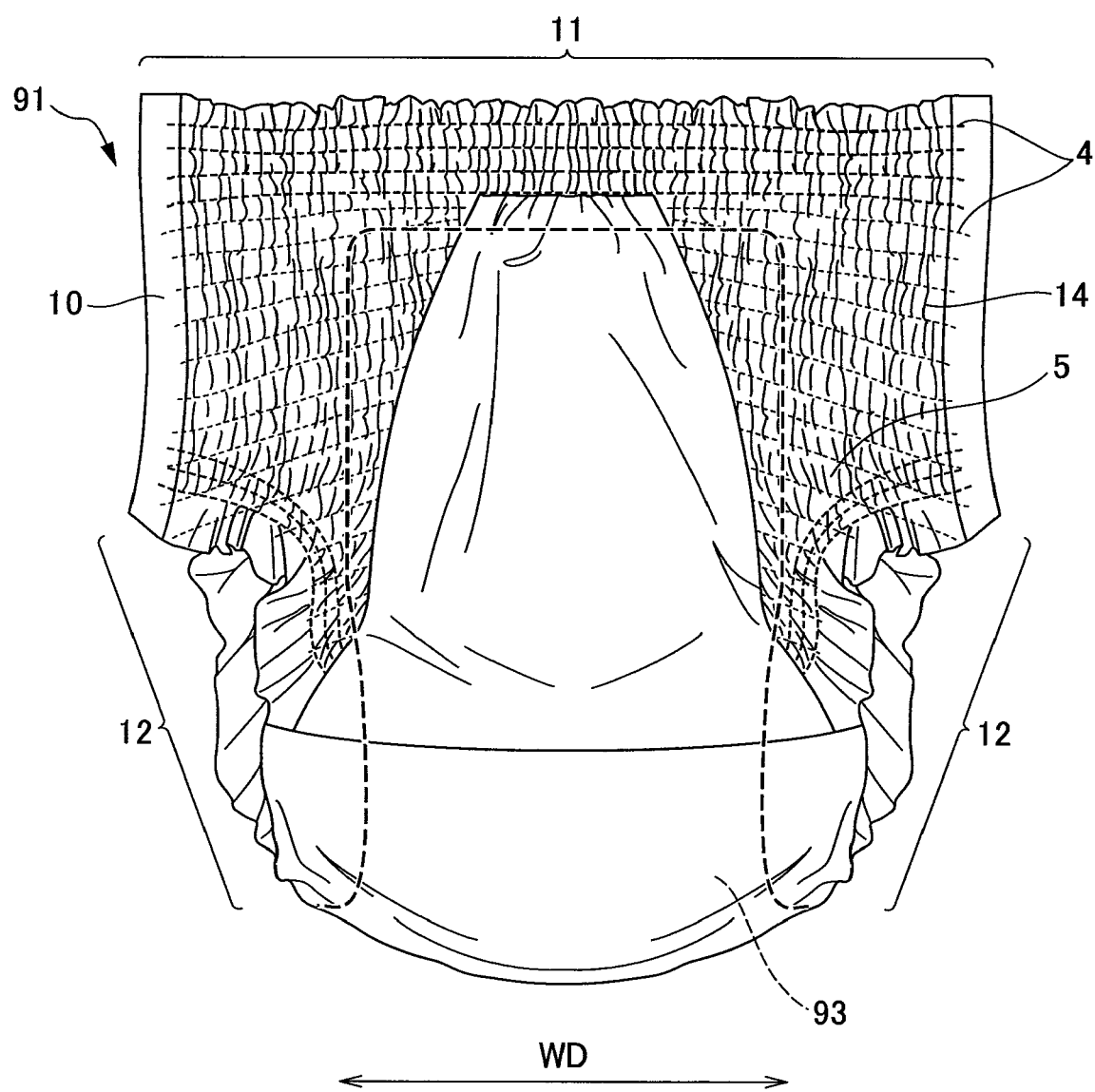
FIG. 8 is a perspective view of the disposable diaper using the sheet member according to the present invention.

Although in the present embodiment, a description is made of the disposable diaper having the torso-surrounding opening 11 and the pair of leg-surrounding openings 12 by joining the front torso-surrounding portion 91 and the rear torso-surrounding portion 92 at the predetermined joint 10 and formed in the shape of shorts, as shown in FIG. 8, the present invention is not limited to the same. For example, the present invention may be used for an unfolded-type disposable diaper that can be worn by locking the front torso-surrounding portion 91 and the rear torso-surrounding portion 92 using a locking member or the like. Alternatively, the present invention may be used for a disposable diaper formed in the shape of shorts, which can be locked by a locking member such as a re-lockable surface fastener, as used for the unfolded-type disposable diaper, at a predetermined joint 10 between a front torso-surrounding portion 91 and a rear torso-surrounding portion 92, is easily unlocked, and can be unfolded and relocked.

The whole chassis 9 may be composed of the sheet member 5. For example, a portion on the absorbent core 8, a trimmed and cut portion of the leg-surrounding opening 12, and so on may not use the sheet member 5 but use a normal nonwoven fabric.

Furthermore, in the present invention, an elastic member 4 and a leakage-prevention wall, i.e., a so-called leg gather (not shown) formed using a leakage-prevention sheet may be arranged along both ends in the width direction WD of the absorbent core 8 in the disposable diaper. Specifically, the leakage-prevention sheet may be provided so as to extend in the width direction WD of the absorbent core 8 from an area between the absorbent core 8 and the chassis 9 or the liquid-impermeable back sheet 7, and at least one elastic member 4 may be arranged at the ends in the width direction WD of the leakage-prevention sheet and fixed thereto with a hot melt adhesive or the like. The leakage-prevention sheet may remain extending in the width direction WD of the absorbent core 8, or may be folded toward the center in the width direction WD of the absorbent core 8 so that a folded portion is arranged on a surface, on the side of the skin touch surface, of the absorbent core 8.

The disposable diaper body is formed in the shape of shorts having the torso-surrounding opening 11 and the pair of leg-surrounding openings 12 by joining the front torso-surrounding portion 91 and the rear torso-surrounding portion 92 at the predetermined joint 10, as shown in FIGS. 7A and 8.

In a case where the disposable diaper is employed for children, exemplified as the vertical length of the main body of the disposable diaper for children, which has not been worn, formed in the shape of shorts, for example, can be 200 mm to 300 mm. Exemplified as the maximum length between the joints 10 in an unfolded state in the width direction WD of the disposable diaper body for children can be 300 mm to 450 mm.

Although the liquid-impermeable back sheet 7 is arranged on a surface, on the side of the non-skin touch surface, of the user, the present invention is not limited to the same. For example, it may be provided between the absorbent core 8 and the chassis 9. Alternatively, it may be provided, when the chassis 9 is formed of a plurality of sheets, between the sheets.

Here, the liquid-permeable top sheet 6 is joined to the absorbent core 8 so as to be affixed to each other with a hot melt adhesive. Further, the liquid-permeable top sheet 6 and the absorbent core 8 are joined to the chassis 9 so as to be affixed to each other with the hot melt adhesive. Similarly, the chassis 9 is joined to the liquid-permeable back sheet 7 so as to be affixed to each other with the hot melt adhesive.

Examples of a coating pattern for hot melt adhesion include spiral coating, control seam coating, coater coating, curtain coater coating, and summit gun coating. It is preferable that the mass per unit area of the adhesives in the hot melt adhesion is preferably 1 g/m$^2$ to 30 g/m$^2$ and more preferably 3 g/m$^2$ to 10 g/m$^2$. Further, in such a pattern that adhesives are applied in a linear shape, the line diameter thereof is preferably 30 μm to 300 μm.

The front torso-surrounding portion 91 and the rear torso-surrounding portion 92 are intermittently joined to each other with ultrasonic sealing at the joint 10. Further, exemplified as another joining method, the attachment can be formed with heat sealing, hot melt adhesives, and others.

As shown in FIGS. 7A and 8, in the disposable diaper body, a plurality of thread-shaped elastic members 4 are arranged in an area around the torso-surrounding opening 11. The elastic member 4 may be in a strip shape. Further, the elastic member 4 may be an elastic sheet having a degree of stretch such as a stretchable nonwoven fabric (e.g., a nonwoven fabric formed of a fiber blend of polyurethane and polypropylene) or a stretchable film.

A sheet member 5 obtained by laminating high-density region-containing sheets 2 obtained by the manufacturing method as shown in FIG. 2 has a groove area 23, to form a stay area. Therefore, it is possible to always promote formation of fine projections and recesses for each predetermined spacing in a shaped area where high-density regions 21 and low-density regions 22 are formed.

In the disposable diaper using the sheet member according to the present invention, the sheet member having the irregular pattern formed therein causes a large number of flexible and small irregular wrinkles (concavities and convexities) to appear when the elastic member contracts. Even in either a state where the elastic member expands or a state where it contracts, therefore, the elastic member is brought into contact with the skin of the user at projections of the irregular pattern. Thus, a disposable diaper that more strongly adheres to the user and which lacks a foreign body sensation while wearing can be provided. Further, the sheet member has a large number of flexible and small irregular wrinkles (concavities and convexities), so that a clearance between the user and the disposable diaper can be reduced, which can prevent excreta or the like from leaking. Further, the sheet member has a large number of flexible and small irregular wrinkles (concavities and convexities), so that the surface area thereof increases, resulting in improved heat insulation properties.

EMBODIMENTS

Although embodiments of the present invention will be described, the embodiments are solely for explaining the present invention and are not intended to limiting the present invention in any way.

Manufacture of High-Density Region-Containing Sheet 2

To obtain a high-density region-containing sheet 2, 19 g/m$^2$ of a polypropylene spunbond (PPSB) and 15 g/m$^2$ of an SMS nonwoven fabric were compressed by shaping rolls 3 each having toothed areas 31 such that the length of high-density regions 21 was 0.45 mm and the length of low-density regions 22 was 1.65 mm. The density of the high-density regions 21 was 0.07 g/cm$^3$ in order to obtain a first rigidity, and the density of the low-density regions 22 was 0.034 g/cm$^3$ in order to obtain a second rigidity.

Manufacture of Sheet Member 5

High-density region-containing sheets 2 previously produced were laminated with a 620 denier elastic member 4 positioned therebetween, where the sheet was stretched to a size two times that of the normal pre-stretched state, to produce a sheet member 5. The pitch of an elastic member 4 was set to 5 mm (hereinafter referred to as a sample 1).

Flexural Property Test

Sample 1, measuring 100 mm by 100 mm, was positioned to be curved in a direction perpendicularly to a machine direction (MD) on a flexural property test machine (KES FB-2 manufactured by KATO TECH CO. LTD.,) of a non-woven fabric, in order to conduct a KES test for the measurement of bending rigidity and hysteresis. These measurements were similarly measured in a cross direction (CD).

For comparison with sample 1, bending rigidity and hysteresis (bending recovery) were similarly measured in comparative examples 1 and 2. The comparative example 1 was manufactured by joining 19 g/m² of PPSB, 15 g/m² of an SMS nonwoven fabric, and a 620 denier elastic member 4 stretched to a size two times that of the time of pre-stretched state, and further performing an embossing processing. The comparative example 2 was produced by joining 19 g/m² of PPSB, 15 g/m² of an SMS nonwoven fabric, and a 620 denier elastic member 4 stretched to a size two times that of the time of pre-stretched state.

Table 1 shows the results of the test.

TABLE 1

|  | Bending rigidity ([×10N · m²/m]K) | Bending recovery rate ([×10N · m²/m]K) |
| --- | --- | --- |
| Sample 1 | 0.0295 | 0.029 |
| Comparative example 1 | 0.0471 | 0.0639 |
| Comparative example 2 | 0.0897 | 0.1202 |

As indicated in Table 1, the bending rigidity of sample 1 is lower than both of the comparative examples 1 and 2, suggesting that sample 1 is less rigid than the comparative examples. Further, the hysteresis of sample 1 also takes the smallest value, which shows that the sample 1 has a higher bending recovery rate than the comparative examples 1 and 2. This suggests that sample 1 has flexible and small irregular wrinkles (concavities and convexities) formed therein and can therefore provide a low degree of skin stimulation.

Functionality Test

Examiners were asked to touch sample 1, the comparative example 1, and the comparative example 2, and respectively evaluate each material on an absolute scale. Table 2 shows the results of the functionality test.

TABLE 2

|  | Very soft | Slightly soft | Normal | Slightly hard | Very hard |
| --- | --- | --- | --- | --- | --- |
| Sample 1 | 7 | 13 | — | — | — |
| Comparative example 1 | — | 5 | 13 | 2 | — |
| Comparative example 2 | — | 3 | 12 | 5 | — |

As indicated in Table 2, sample 1 scored a greater number of results in the very soft and slightly soft categories compared to that of the results for the comparative examples 1 and 2, suggesting that sample 1 is softer than the comparative examples. Consequently, it can be suggested that sample 1 is more pleasant to touch and provides less skin stimulation, compared to the comparative example 1 and comparative example 2.

The invention claimed is:

1. A sheet member, comprising:
a first sheet;
a second sheet; and
at least one elastic member having a shape selected from a thread shape, a net shape, a strip shape, and a sheet shape, arranged between the first sheet and the second sheet;
wherein
the first sheet comprises:
a plurality of high-density regions; and
a plurality of low-density regions, wherein the high-density regions alternate with the low-density regions in a predetermined direction,
the elastic member is arranged in the predetermined direction in which the plurality of high-density regions alternate with the plurality of low-density regions,
the elastic member in an expanded state is attached to at least a part of each of the plurality of high-density regions, and
the following equation is satisfied:

$$(A+C)/X \geq A$$

wherein A is a length of the high-density region, C is a length of the low-density region, and X is a substantial expansion magnification of the elastic member.
2. The sheet member according to claim 1, wherein at least the first sheet is formed to have concavities and convexities, in the predetermined direction, in the sheet member.
3. The sheet member according to claim 1, wherein the density of the high-density region is 0.05 to 0.6 g/cm³ in order to obtain a first rigidity.
4. The sheet member according to claim 1, wherein the density of the low-density region is 0.01 to 0.05 g/cm³ in order to obtain a second rigidity.
5. The sheet member according to claim 1, wherein the length of the high-density region is 0.1 to 1.5 mm in the sheet member.
6. The sheet member according to claim 1, wherein the length of the low-density region is 0.5 to 3 mm in the sheet member.
7. The sheet member according to claim 1, wherein the elastic member is coated with an adhesive, and is attached to the first sheet and the second sheet of the sheet member, to join the elastic member and the high-density regions to each other.
8. A disposable diaper, comprising:
a chassis composed of a front torso-surrounding portion and a rear torso-surrounding portion, and having a torso-surrounding opening and a pair of right and left leg-surrounding openings positioned in an under-crotch portion;
a liquid-permeable top sheet disposed in at least a part of the chassis;
a liquid-impermeable back sheet disposed on a first side, in the thickness direction, of the liquid-permeable top sheet; and
an absorbent core, having liquid holding properties, disposed between the liquid-permeable top sheet and the liquid-impermeable back sheet,
a sheet member is disposed in an area between the torso-surrounding opening and the leg-surrounding openings of the chassis, wherein the sheet member includes
a first sheet;
a second sheet; and at least one elastic member having a shape selected from a thread shape, a net shape, a strip shape, and a sheet shape, arranged between the first sheet and the second sheet;
wherein
the first sheet comprises:
 a plurality of high-density regions; and
 a plurality of low-density regions, wherein the high-density regions alternate with the low-density regions in a predetermined direction,
the elastic member is arranged in the predetermined direction in which the plurality of high-density regions alternate with the plurality of low-density regions,
the elastic member in an expanded state is attached to at least a part of each of the plurality of high-density regions, and
the following equation is satisfied:

$$(A+C)/X \geqq A$$

wherein A is a length of the high-density region, C is a length of the low-density region, and X is a substantial expansion magnification of the elastic member.

* * * * *